United States Patent
Hashimoto et al.

[11] Patent Number: 6,090,412
[45] Date of Patent: Jul. 18, 2000

[54] H₂-RECEPTOR ANTAGONIST AND ANTACID COMPOSITION

[75] Inventors: Yoshimi Hashimoto; Hiroyoshi Shiozawa; Hideyuki Kishimoto; Yoichi Setoguchi, all of Shizuoka, Japan

[73] Assignee: Yamaouchi Pharmaceutical Co., Ltd., Tokyo, Japan

[21] Appl. No.: 09/077,186

[22] Filed: May 26, 1998

[30] Foreign Application Priority Data

Nov. 27, 1995 [JP] Japan ................................. 7-307512

[51] Int. Cl.⁷ ............................. A61K 9/16; A61K 9/36; A61K 9/32

[52] U.S. Cl. .................... 424/490; 424/480; 424/482; 424/497; 424/494; 424/495; 424/400

[58] Field of Search ...................... 424/479, 480, 424/482, 474, 475, 497, 494, 495, 490, 400

[56] References Cited

U.S. PATENT DOCUMENTS 5,409,709  4/1995  Ozawa et al. ............................ 424/464

FOREIGN PATENT DOCUMENTS

| | | | |
|---|---|---|---|
| 0 286 781 | 10/1988 | European Pat. Off. | |
| 0 338 861 | 10/1989 | European Pat. Off. | A61K 9/26 |
| 0 638 313 | 2/1995 | European Pat. Off. | A61K 33/10 |
| 3-44319 | 2/1991 | Japan | A61K 9/58 |
| 6-56677 | 3/1994 | Japan | A61K 33/06 |
| 6-239756 | 8/1994 | Japan | A61K 33/08 |
| 92/17161 | 10/1992 | WIPO | A61K 9/00 |
| 95/16446 | 6/1995 | WIPO | |
| 95/33469 | 12/1995 | WIPO | A61K 33/06 |

OTHER PUBLICATIONS

International Search Report.

*Primary Examiner*—Thurman K. Page
*Assistant Examiner*—Todd D Ware
*Attorney, Agent, or Firm*—Sughrue, Mion, Zinn, Macpeak & Seas, PLLC

[57] ABSTRACT

A solid pharmaceutical composition for oral administration comprising a histamine H₂-receptor antagonist, a low neutralizing capacity antacid, and a high neutralizing capacity antacid coated with a pH-independent and water-insoluble polymer base, which composition improves the condition of a patient promptly after administration and sustains the effects for an extended period of time in the treatment of digestive disorders on which suppression of gastric acid secretion is effective.

9 Claims, 3 Drawing Sheets

H₂-RECEPTOR ANTAGONIST AND ANTACID COMPOSITION

TECHNICAL FIELD

This invention relates to a solid pharmaceutical composition for oral administration which comprises a combination of a histamine $H_2$-receptor antagonist and a novel antacid component.

BACKGROUND ART

Suppression of gastric acid which attacks the gastric mucosa is effective in the treatment of digestive disorders, such as gastritis, dyspepsia, gastric hyperacidity, heartburn, gastric oppression, and peptic ulcer. Antacids, histamine $H_2$-receptor antagonists, anticholinergics, antigastrins, muscarine receptor antagonists, proton pump inhibitors, etc. have been used for this purpose.

The histamine $H_2$-receptor antagonists, for example, cimetidine, ranitidine, nizatidine and famotidine, antagonize histamine at the $H_2$-receptors of stomach cells to inhibit gastric acid secretion. The antacids directly neutralize the gastric acid that has been secreted or is being secreted.

Hence, simultaneous administration of a histamine $H_2$-receptor antagonist and an antacid is expected to produce high therapeutic effects, immediately neutralizing the secreted gastric acid while inhibiting gastric acid secretion, thereby complementarily eliminating gastric acid, which is a large cause of stimulation on the gastric mucosa.

Combinations of histamine $H_2$-receptor antagonists and antacids are taught in the following literature.

German Patent 3710462 teaches a pharmaceutical composition containing a histamine $H_2$-receptor antagonist and an antacid and having a cell protecting activity, showing a suspension containing 0.4 g of cimetidine, 6.3 g of aluminum hydroxide gel, and 1.5 g of magnesium hydroxide per 10 ml.

PCT International Publication Pamphlet 92/00102 and 93/12779 disclose tablet, etc. containing 2 mg of famotidine, 750 mg of aluminum hydroxide, and 750 mg of magnesium hydroxide as a pharmaceutical composition comprising a histamine $H_2$-receptor antagonist and an antacid, which has its equilibrium pH, acid neutralizing capacity and gastric duration optimally adjusted so as to have a pH level substantially equal to the pH level based on the pKa value of the histamine $H_2$-receptor antagonist.

PCT International Publication Pamphlet 93/21932 teaches the effect of a combined use of 400 mg of cimetidine and 30 ml of Maalox Plus oral liquid (magnesium hydroxide and aluminum hydroxide) on a patient suffering from heartburn.

An unexamined published Japanese patent application No. 7-165596 discloses tablets each containing 31.5 mg of ranitidine hydrochloride, 125 mg of magnesium aluminium silicate, 100 mg of magnesium aluminate, and 50 mg of magnesium oxide as a pharmaceutical composition for oral administration containing ranitidine or a pharmaceutically acceptable salt thereof, magnesium aluminium silicate, magnesium aluminate, and magnesium oxide.

Histamine $H_2$-receptor antagonists gradually increase the gastric pH when orally administered. Taking famotidine for an instance, after 20 mg is orally given, the pH gradually rises, reaches a plateau at pH 6 after about 3 hours, and is maintained in the range of from 5 to 6 over about 9 hours (Ikezoe, et al., *Dai 12-kai kokusai syokakibyo gakkai*). Antacids, which are a kind of alkali, neutralize gastric acid through acid-alkali reaction immediately after administration.

Therefore, it is desirable for the antacid to be combined with a histamine $H_2$-receptor antagonist to be capable of neutralizing gastric acid immediately after administration and retaining the gastric pH within an optimum range of from 3 to 5 for at least about 3 hours' duration, by the end of which the histamine $H_2$-receptor will have come to manifest its full effects. However, an excessive pH rise, especially in the initial pH immediately after administration is unfavorable because of the possibility of inducing gastric acid secretion as a rebound phenomenon (refer to Goodman and Gilman (ed.), *The pharmacological Basis of Therapeutics* of 7th Ed., pp 1209–1219, Hirokawa Shoten (May 25, 1988)).

That is, it has been demanded to develop a pharmaceutical composition in which an $H_2$-receptor antagonist is combined with such an antacid as (1) exerts a prompt neutralizing action without increasing the initial pH immediately after administration more than necessary and (2) sustains the optimum pH of 3 to 5 for about 3 hours, duration from administration, whereby the conditions of a patient will be improved promptly, and the effects will last for more than half a day.

However, none of the solid preparations comprising a histamine $H_2$-receptor antagonist and an antacid that have been reported to date satisfies: the above requirements.

DISCLOSURE OF THE INVENTION

The present invention relates to a solid pharmaceutical composition for oral administration characterized by containing a histamine $H_2$-receptor antagonist and, as antacid components, a low neutralizing capacity antacid and a high neutralizing capacity antacid which is coated with a pH-independent and water-insoluble polymer base.

While a combination of a low neutralizing capacity antacid and a high neutralizing capacity antacid is generally employed, solid antacid preparations obtained by merely combining them fail to fulfill the above-described two requirements. That is, a preparation designed to have extended duration of an optimum pH would raise the initial pH excessively, whereas a preparation containing a reduced amount of the high neutralizing capacity antacid for controlling the initial pH rise would be of short duration.

The language "excessive rise in initial pH" and similar expressions as used herein mean that the initial pH immediately after administration rises too much, reaching such a pH range that induces gastric acid secretion by reflex for biophylaxis. It is difficult to clearly define the initial pH range which would induce gastric acid secretion because such a range differs with patients. In general, such a pH range means a range of 6 or higher when measured in the initial stage (within 10 minutes from addition of a drug) of a testing system using an artificial gastric juice model according to the modified Fuchs method, which is regarded as a model clinically close to the conditions in the stomach. The modified Fuchs method is a testing method of antacid capacity using the artificial gastric juice model described in Yamagata et al., *Koso to rinsyo*, Vol. 24, No. 10, pp. 1023–1028 (1990).

The inventors of the present invention coated a high neutralizing capacity antacid with a polymer which is insoluble in water and whose solubility is independent on pH (hereinafter referred to as a pH-independent and water-insoluble polymer base or simply as a polymer base) thereby to control the dissolution of the antacid and combined the coated high neutralizing capacity antacid with a low neutralizing capacity antacid. As a result, they have succeeded in providing an antacid combination satisfying the above-described two requirements. By mixing this antiacid combination with a histamine $H_2$-receptor antagonist, the present invention was accomplished.

The combination of a low neutralizing capacity antacid and a polymer base-coated high neutralizing capacity antacid which is used in the pharmaceutical composition of the present invention, when tested in an artificial gastric juice model according to the modified Fuchs method, neutralizes gastric acid immediately after addition to adjust to an optimum pH without causing an excessive rise in initial pH and sustains the effect for more than 3 hours.

In the present invention, the antacid components continue neutralizing gastric acid being secreted to maintain the gastric pH at an optimum level for at least about 3 hours' duration, by the end of which the histamine $H_2$-receptor will have been absorbed to produce its effects. After the end of the 3 hours' duration when the effects of the antacid components begin to disappear, the absorbed $H_2$-receptor antagonist suppresses gastric acid secretion over a long period of time. In other words, the present invention provides a useful pharmaceutical composition that can maintain an optimum gastric pH from immediately after the administration for more than half a day.

The present invention will be described in greater detail.

The histamine $H_2$-receptor antagonists which can be used in the present invention include cimetidine, ranitidine, nizatidine, and famotidine but are not limited thereto. Pharmaceutically acceptable salts of these drugs are also included. Useful salts include those formed with organic or inorganic acids, such as a hydrochloride, a hydrobromide, a hydroiodide, a sulfate, a fumarate, a maleate, a succinate, a tartrate, and a picrate. Of the histamine $H_2$-receptor antagonists particularly preferred is famotidine whose inhibitory effect on gastric acid secretion is the longest in duration.

The high neutralizing capacity antacid usable in the present invention is not particularly limited as long as it gives an initial pH of 6 or higher when a single dose thereof as an antacid is added to 30 ml of 0.05N hydrochloric acid and tested by the modified Fuchs method. The term "single dose" as used herein denotes a third of the maximum daily dose described in *Iyakuhin seizo shishin* specified by Japanese Ministry of Health and Welfare (edited by Nippon Koteisho Kyokai, 1992-edition) (the same applies hereinafter). Particularly preferred examples include sodium compound antacids such as sodium hydrogencarbonate; magnesium compound antacids such as magnesium oxide, magnesium hydroxide, magnesium carbonate, and magnesium silicate; and calcium compound antacids such as calcium carbonate. The magnesium compound antacids are still preferred. Particularly preferred of them is magnesium hydroxide which has been used long (20 years or more) enough to confirm its safety.

The low neutralizing capacity antacid which can be used in the present invention is not particularly limited as long as it gives an initial pH lower than 6 when a single dose thereof as an antacid (a third of the maximum daily dose described in *Iyakuhin seizo shishin*) is added to 30 ml of 0.05N hydrochloric acid and tested by the modified Fuchs method. Preferred examples include aluminum-magnesium composite compound antacids such as magnesium aluminate, magnesium aluminosilicate hydrate, aluminium magnesium silicate, bismuth magnesium aluminosilicate hydrate and synthetic hydrotalcite, and aluminum compound antacids such as dried aluminum hydroxide gel and aluminum silicate. The aluminum compound antacids are still preferred. Particularly preferred of them is dried aluminum hydroxide gel which has been used long (20 years or more) enough to confirm its safety.

Two or more of the high neutralizing capacity antacids and/or two or more of the low neutralizing capacity antacids can be used in combination.

The histamine $H_2$-receptor antagonist can be used at a usual and clinically acceptable dose level. There are various histamine $H_2$-receptor antagonists having respective adequate doses. For example, cimetidine is usually administered at a daily dose of 800 mg in a single or 2 to 4 divided doses for ulcer, etc. or a daily dose of 400 mg in 2 to 4 divided doses for gastritis, etc. These daily doses are preferably somewhat varied according to the symptoms. A recommended daily dose of famotidine ranges from 0.5 mg to 500 mg, given in a single dose or 2 to 4 divided doses, particularly 1 mg to 100 mg in a single dose or 2 to 4 divided doses.

The total amount of the antacid components, i.e., the low neutralizing capacity antacid and the high neutralizing capacity antacid coated with a pH-independent and water-insoluble polymer base is not particularly limited as far as (1) a prompt neutralizing action is exerted without excessively increasing the initial pH and (2) the optimum pH is maintained for a certain duration. It is desirable for the antacid components to have such antacid capacity as consumes not less than 50 ml of 0.1N hydrochloric acid per day in the antacid capacity test method according to *Japanese Pharmacopeia*. It is preferable that the total amount of the antacid components be not such that increases the pH of the artificial gastric juice to an alkaline region exceeding 7 when tested by the modified Fuchs method.

The amounts of the low neutralizing capacity antacid and the coated high neutralizing capacity antacid vary depending on various conditions, such as the kinds of the antacids, the kind and amount of the coating polymer base, and whether or not an uncoated high neutralizing capacity antacid is used in combination. Therefore they cannot be defined generally, but it is preferred for achievement of the object of the present invention that the mixing ratio of the low neutralizing capacity antacid to the high neutralizing capacity antacid "per se" be 0.2:1 to 2:1.

The amounts of antacid components will be described in more detail taking, for instance, a combination of magnesium hydroxide as a high neutralizing capacity antacid and dried aluminum hydroxide gel as a low neutralizing capacity antacid, which has been proved to be a particularly favorable embodiment of the present invention.

The "dried aluminum hydroxide gel" contains at least 50.0% of aluminum oxide as described in *Japanese Pharmacopeia* XII. The purity of dried aluminum hydroxide gel varies among lots of the raw material. Therefore in what follows the amount of dried aluminum hydroxide gel is expressed in terms of its aluminum oxide content.

The most preferred amounts (doses) of magnesium hydroxide and dried aluminum hydroxide gel are about 400 mg and about 225 mg (in terms of aluminum oxide), respectively. These doses have been confirmed to be safe as a result of their use for more than 20 years as liquid preparations for oral administration. These doses can be somewhat increased or decreased according to the symptoms of a patient and the like. When 400 mg of magnesium hydroxide and 225 mg, in terms of aluminum oxide, of dried aluminum hydroxide gel are to be combined, the portion of magnesium hydroxide (i.e., a high neutralizing capacity antacid) to be coated with a pH-independent and water-insoluble polymer base is about 300 to 400 mg. This is because presence of more than 100 mg of uncoated magnesium hydroxide results in an excessive rise in initial pH (see Test Example 2).

The magnesium hydroxide to aluminum oxide mixing ratio is preferably about 1:0.56 for the same reasons. This ratio can be increased or decreased appropriately according to the symptoms of a patient and the like. At this mixing ratio, the proportion of magnesium hydroxide to be coated with the polymer base is preferably 75% or more.

The pH-independent and water-insoluble polymer base which can be used in the present invention is not particularly limited as far as it is pharmaceutically acceptable and so water-insoluble as to achieve the object of the present invention, and has pH-independent solubility. Examples thereof include ethyl cellulose, an aqueous dispersion of ethyl cellulose (e.g., Aquacoat, produced by FMC Inc.), polyethylacrylate methylmethacrylate trimethylammonioethylmethacrylate chloride (e.g., Eudragit RS100 and RS30D, produced by Rhohn Pharma), and ethyl acrylate-methyl methacrylate copolymer emulsions (e.g., Eudragit NE30D, produced by Rhon Pharm). These polymers can be used in either individually or in combination of two or more thereof. A mixture of an aqueous dispersion of ethyl cellulose and an ethyl acrylate-methyl methacrylate copolymer emulsion is particularly preferred. If desired, the coating composition of the polymer base may contain plasticizers, lubricants, defoaming agents, colorants, surface active agents, and the like.

A solvent which can be used in the coating composition is not particularly limited as long as it is pharmaceutically acceptable and capable of dissolving or dispersing the above-described polymer base. Suitable examples include water and organic solvents, such as methanol, ethanol, isopropyl alcohol, methylene chloride, hexane, and acetone. These solvents can be used either individually or in combination of two or more thereof. The concentration of the polymer base dissolved or dispersed in the solvent is generally 30% by weight or less, while varying depending on the combination of the polymer and the solvent.

Coating of the high neutralizing capacity antiacid with the polymer base can be carried out in a customary method. For example, the high neutralizing capacity antiacid (e.g., magnesium hydroxide), either alone or in combination with an excipient such as lactose, is mixed with an aqueous solution of hydroxypropyl cellulose as a binder, ground, and dried by means of a stirring granulator, followed by sieving, for example through a sieve of 24 mesh, to obtain granules. The granules are then put into a fluidized bed coating machine, where a coating solution is sprayed thereto to a desired coating weight.

Alternatively, magnesium hydroxide, crystalline cellulose, and polyvinylpyrrolidone are charged in a high-speed granulator, and purified water is added thereto. The mixture is granulated to obtain spherical granules and dried. The resulting granules are charged in a fluidized bed coating machine, and a coating solution is sprayed thereto to a desired coating weight.

In another method, magnesium hydroxide, lactose, and starch are charged in a stirring granulator and kneaded with a polyvinylpyrrolidone aqueous solution as a binder, and the mixture is extruded into cylindrical granules by means of an extrusion granulator, which are then rounded in a centrifugal fluid granulator, followed by drying to obtain granules. The resulting granules are then coated in a centrifugal fluid granulator in the same manner as described above.

In addition, coating may be carried out by a method comprising atomizing a paste of magnesium hydroxide in a binder solution into spherical particles by means of a spray drier and coating the resulting particles or a method comprising granulating a mixture of magnesium hydroxide and a coating solution and, if desired, an excipient by means of a fluidized bed granulator and coating the resulting granules.

Coating can also be effected by a method in which core particles of crystalline cellulose or sucrose are coated with a mixture a binder solution and magnesium hydroxide powder or a dispersion of magnesium hydroxide in a centrifugal fluid granulator, and the resulting granules are coated.

There are various coating techniques as mentioned above, from which the most suitable one is to be chosen for considerations of workability and cost. The present invention is by no means limited by the above-described coating methods.

The coating amount of the polymer base as dissolved or dispersed in a solvent cannot be generally defined because it depends on the combination of the solvent and the polymer base and the form, particularly the particle size, of the granules to be coated. The amount is about 5 to 20% by weight for those granules having a particle size on a granule level and about 20 to 100% by weight for smaller ones.

Although the high neutralizing capacity antiacid is coated with the polymer base, there are gaps among many coating layers and strains in the molecular chains of the coating polymer base, which offer paths for letting water in or the antacid out. The coated antacid can be thus released.

The two requirements, i.e., duration of an optimum pH and avoidance of an excessive rise in initial pH, can be met by combining the polymer base-coated high neutralizing capacity antiacid and the low neutralizing capacity antiacid. These antacid components and the histamine $H_2$-receptor antagonist are formulated together with other necessary components into solid pharmaceutical compositions. Specifically, the antacid components and the histamine $H_2$-receptor antagonist are mixed with excipients and other components having an activity as a pharmaceutical, and, if necessary, disintegrants, binders, lubricants, fluidizing agents, flavors, colorants, stabilizers, coating agents, and the like, and the composition is formed into tablets, chewable tablets, granules, powders, fine granules, pills or capsules in a conventional manner. Suitable excipients include mannitol, lactose, starch, xylitol, erythritol, and sorbitol.

For example, the histamine $H_2$-receptor antagonist (e.g., famotidine), a low neutralizing capacity antiacid (e.g., dried aluminum hydroxide gel), an excipient (e.g., lactose or starch) and, if necessary, other active ingredients and additives are granulated in a fluidized bed granulator by using a binder such as hydroxypropylmethyl cellulose, and the polymer base-coated high neutralizing capacity antiacid (e.g., magnesium hydroxide) is mixed therewith to prepare granules, fine granules or powders. Tablets or chewable tablets are obtained by adding a lubricant to the above-prepared particulate mixture and tableting the mixture through a rotary tableting machine. Capsules are obtained by charging the mixture in capsule containers in a conventional manner.

In preparing these solid pharmaceutical compositions, a high neutralizing capacity antiacid which is not coated with a polymer base can be used in addition to, or in place of part of, the polymer base-coated high neutralizing capacity antacid to control the duration of the antacid components in such an amount that would not cause an excessive rise of the initial pH.

The pharmaceutical composition of the present invention can contain other ingredients having pharmaceutical activities, such as antimicrobials against *Helicobacter pylori*, e.g., amoxicillin, minocycline, erythromycin, and ofloxacin; enterokinesis accelerators, e.g., trimebutine maleate, cisapride, and domperidone; prostaglandin, sucralfate, gefarnate, cetraxate, teprenone, and benexate hydrochloride betadex. Further included in useful ingredients are stomachic crude ingredients, such as swertia herb, cinnamon bark, l-menthol, and dl-menthol; gastroenteric function regulators, such as carnitine chloride and bethanechol chloride; stomachics, such as dry yeast; amino acid agents, such as aminoacetic acid and dihydroxyaminoaluminum acetate; anticholinergics, such as scopolia extract, atropine, scopolamine, isopropamide, and benactyzine methobromide; digestive enzymes, such as starch digesting enzyme, protein digesting enzyme, and cellulose digesting enzyme; digestives, such as cholagogues, e.g., ursodesoxycholic acid, oxycholanoates, cholic acid, bile powder, pile extract (powder), dehydrocholic acid, and animal bile (including bear bile); intestine regulating agents, such as viable microorganism ingredients; adsorbents, such as kaolin, natural aluminum silicate, and aluminum hydroxynaphthoate; antidiarrheics, such as coating agents, e.g., precipitated calcium carbonate and calcium lactate; mucosa repairing agents, such as sodium azulenesulfonate, aldioxa, glycyrrhizic acid and salts thereof, licorice extract, L-glutamine, potassium copper chlorophillin, histidine hydrochloride, pepsin degradation products of porcine stomach, methylmethioninesulfonium chloride, malloti cortex, and corydalis tuber; and defoaming agents, such as dimethyl polysiloxane.

BEST MODES FOR CARRYING OUT THE INVENTION

Figure 1:
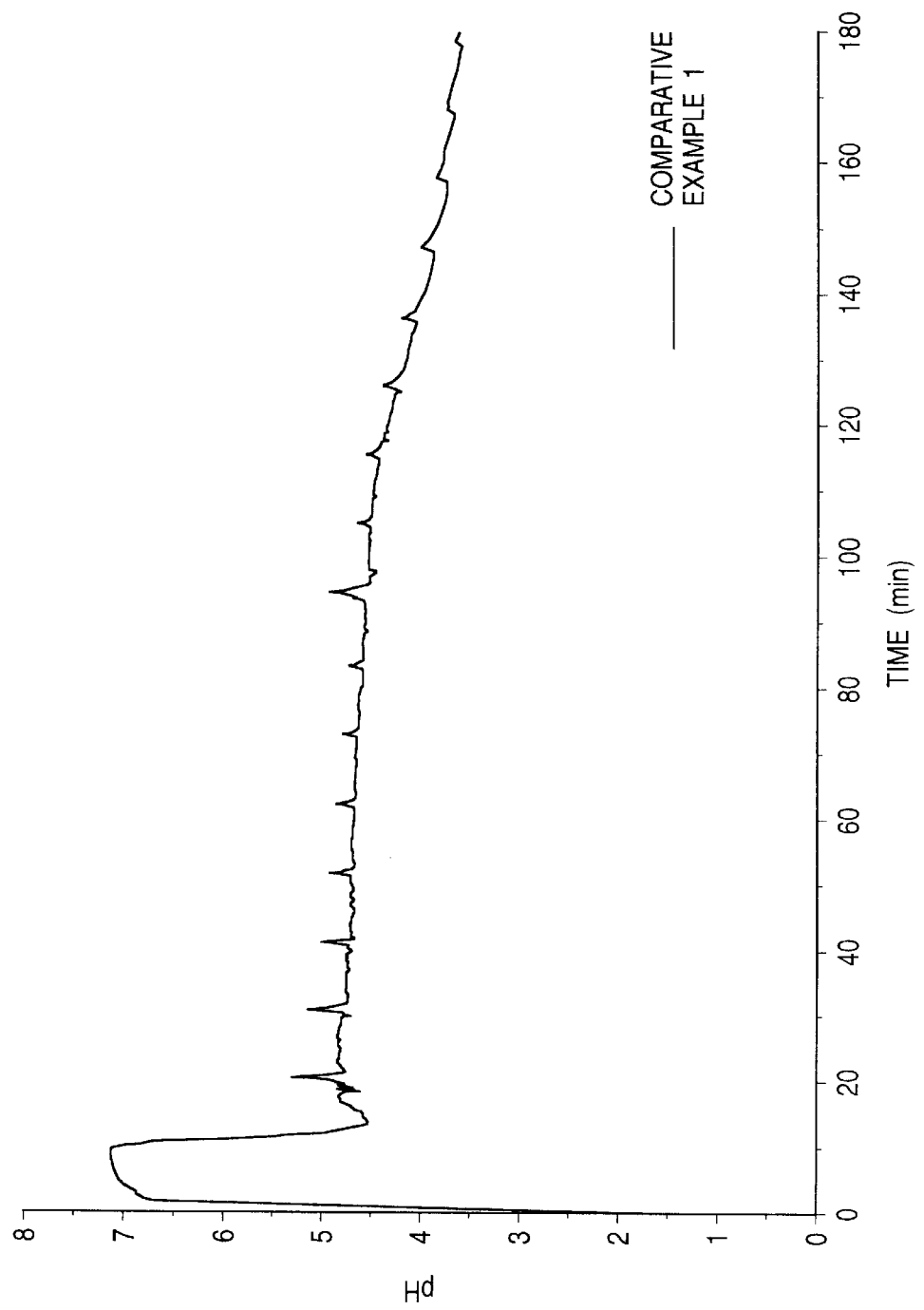
FIG. 1 illustrates the results of testing the duration of the antiacid capacity of the chewable tablet obtained in Comparative Example 1 in an artificial gastric juice model according to the modified Fuchs method.

The present invention will now be illustrated in greater detail by way of the examples of the solid pharmaceutical composition for oral administration according to the present invention, but the present invention should not be construed as being limited thereto.

COMPARATIVE EXAMPLE 1

In a fluidized bed granulator FLO-1 were charged 100 parts of magnesium hydroxide, 103 parts of dried aluminum hydroxide gel, 1.25 part of famotidine, 120 parts of mannitol, 50 parts of lactose, and 47.3 parts of starch and granulated by using 180 parts of a 7.5% aqueous solution of hydroxypropyl cellulose (HPC). The resulting granules were mixed with 2.25 parts of light silicic anhydride, 0.45 part of a flavor, 13.5 parts of magnesium stearate, and 1.25 part of famotidine, and the mixture was tableted by means of a rotary tableting machine to obtain chewable tablets each weighing 1.8 g, measuring 18 mm in diameter, and containing 400 mg of magnesium hydroxide, 412 mg of dried aluminum hydroxide gel (corresponding to 225 mg of aluminum oxide), and 5 mg of famotidine.

EXAMPLE 1

In a fluidized bed granulator FLO-1, 500 part of magnesium hydroxide was granulated and subsequently coated with a coating solution of 150 parts of ethyl cellulose in 1350 parts of ethanol under conditions of 50° C. in spray air temperature, 2.0 kg/cm² in spray air pressure, and 9 g/min in flow rate to obtain coated magnesium hydroxide granules having a coating weight of 10, 15 or 20% on a solid basis.

EXAMPLE 2

A mixture of 137.3 parts of dried aluminum hydroxide gel and 180 parts of mannitol was sieved through a 28-mesh sieve, charged in a fluidized bed granulator FLO-1 together with 49.5 parts of lactose and 45.6 parts of starch, and granulated by using 177.3 parts of a 7.5% HPC aqueous solution. Then, 354.7 parts of the resulting granules, 133.3 parts of the 20% coated-granules obtained in Example 1, 28.6 parts of cimetidine, 0.5 part of a flavor, 1.5 parts of silicic anhydride, and 10 parts of magnesium stearate were mixed in a mixer for 15 minutes. The mixture was punched with a rotary tableting machine to obtain chewable tablets each weighing 1.9 g, measuring 18 mm in diameter, and containing 400 mg of magnesium hydroxide, 412 mg of dried aluminum hydroxide gel (corresponding to 225 mg of aluminum oxide), and 100 mg of cimetidine.

EXAMPLE 3

In a fluidized bed granulator FLO-1, 400 part of magnesium hydroxide was granulated and subsequently coated with a coating composition comprising 1000 parts of an aqueous dispersion of ethyl cellulose (Aquacoat, a trade name) and 75 parts of triethyl citrate under conditions of 90° C. in spray air temperature, 1.5 kg/cm² in spray air pressure, and 8 g/min in flow rate to obtain coated magnesium hydroxide granules having a coating weight of 40% on a solid basis. In the same manner as in Example 2 chewable tablets were obtained, each containing 400 mg of magnesium hydroxide, 412 mg of dried aluminum hydroxide gel (corresponding to 225 mg of aluminum oxide), and 150 mg of ranitidine hydrochloride.

EXAMPLE 4

Coated magnesium hydroxide granules having a coating weight of 40% on a solid basis were prepared in the same manner as in Example 3 except for using a coating composition comprising 560.1 parts of an ethyl acrylate-methyl methacrylate copolymer emulsion (Eudragit NE30D, a trade name) and 240 parts of an aqueous dispersion of ethyl cellulose (Aquacoat). Chewable tablets were obtained in the same manner as in Example 2, each containing 400 mg of magnesium hydroxide, 412 mg of dried aluminum hydroxide gel (corresponding to 225 mg of aluminum oxide), and 150 mg of nizatidine.

EXAMPLE 5

Coated magnesium hydroxide granules having a coating weight of 60% on a solid basis were prepared in the same manner as in Example 3 except for using a coating composition comprising 560.1 parts of Aquacoat and 240 parts of Eudragit NE30D. Chewable tablets were obtained in the same manner as in Example 2, each containing 400 mg of magnesium hydroxide, 412 mg of dried aluminum hydroxide gel (corresponding to 225 mg of aluminum oxide), and 1 mg of famotidine.

EXAMPLE 6

A mixture of 175.9 parts of dried aluminum hydroxide gel, 4.3 parts of famotidine, 173.7 parts of lactose, and 43.4 parts of starch was sieved through a 28-mesh sieve and granulated in a fluidized bed granulator FLO-1 by using 100 parts of a 7.0% HPC aqueous solution, followed by sieving through a 32-mesh sieve. Then, 312.3 parts of the resulting granules, 186.7 parts of the 40% coated-granules obtained in Example 4, and 1.0 part of silicic anhydride were mixed in a mixer for 15 minutes to give powder containing 10 mg of famotidine, 400 mg of magnesium hydroxide, and 412 mg of dried aluminum hydroxide gel (corresponding to 225 mg of aluminum oxide) per 1.5 g.

EXAMPLE 7

A mixture of 109.9 parts of dried aluminum hydroxide gel, 20.0 parts of ranitidine hydrochloride, 105.1 parts of lactose, and 45.0 parts of starch was sieved through a 28-mesh sieve. The mixture and 128 parts of the 20%-coated granules obtained in Example 1 were put in a fluidized bed granulator FLO-1 and granulated by using 120 parts of a 10% HPC aqueous solution, followed by sieving through a 12-mesh sieve to give granules containing 75 mg of ranitidine hydrochloride, 400 mg of magnesium hydroxide, and 412 mg of dried aluminum hydroxide gel (corresponding to 225 mg of aluminum oxide) per 1.5 g.

EXAMPLE 8

Into a stirring granulator were put 400 parts of magnesium hydroxide, 150 parts of lactose, and 50 parts of starch, and 120 parts of a 15% HPC aqueous solution was added thereto. The mixture was kneaded and granulated through an extrusion granulator having a nozzle diameter of 0.8 mm. The granules were rounded in a centrifugal fluid granulator and dried to prepare cylindrical granules. Five hundred parts of the granules were charged in a fluidized bed granulator FLO-1 and coated with a coating solution of 30 parts of ethyl cellulose in 270 parts of ethanol to give a coating weight of 7% on a solid basis.

Separately, 412 parts of dried aluminum hydroxide gel, 75.0 parts of nizatidine, 281.9 parts of lactose, and 120.8 parts of starch were put into a stirring granulator and kneaded with 160 parts of a 15% HPC aqueous solution. The mixture was granulated through an extrusion granulator to obtain cylindrical granules. The coated granules of magnesium hydroxide (132.3 parts) and 166.7 parts of the granules containing dried aluminum hydroxide were mixed in a mixer for 10 minutes to obtain granules containing 75 mg of nizatidine, 400 mg of magnesium hydroxide, and 412 mg of dried aluminum hydroxide gel (corresponding to 225 mg of aluminum oxide) per 1.5 g.

EXAMPLE 9

In a fluidized bed granulator FLO-1, 500 part of magnesium hydroxide was granulated and subsequently coated with a coating solution of 150 parts of ethyl cellulose in 1350 parts of ethanol under conditions of 50° C. in spray air temperature, 2.0 kg/cm² in spr7ay air pressure, and 9 g/min in flow rate to obtain coated magnesium hydroxide granules having a coating weight of 20% on a solid basis. Separately, 500 parts of dried aluminum hydroxide gel and famotidine were granulated in a fluidized bed granulator FLO-1 by using 150 pats of a 10% HPC aqueous solution as a binder. The coated magnesium hydroxide (480 parts), 424.4 parts of the dried aluminum hydroxide gel granules, 0.62 part of famotidine, and 4.5 parts of magnesium stearate were mixed, and No. 1 capsules were each filled with 306 mg of the mixture by means of a Hebriger capsule filling machine to give capsules each containing 133.3 mg of magnesium hydroxide, 137.3 mg of dried aluminum hydroxide gel, and 2.5 mg of famotidine.

EXAMPLE 10

Into a fluidized bed granulator FLO-1 were put 400 parts of dried aluminum hydroxide gel and 0.43 parts of famotidine and granulated with 124.5 parts of 10% HPC as a binder. The resulting granules (86.7 parts), 130.6 parts of the 60%-coated magnesium hydroxide prepared in Example 5, 63.3 parts of crystalline cellulose, 15 parts of partially alphanized starch, 3 parts of talc, and 1.5 parts of magnesium stearate were mixed in a mixer for 10 minutes. The mixture was punched by means of a tableting machine into elliptical tablets each weighing 0.491 g, measuring 16 mm in major diameter and 7 mm in minor diameter, and containing 133.3 mg of magnesium hydroxide, 137.3 mg of dried aluminum hydroxide gel, and 1.25 mg of famotidine.

INDUSTRIAL APPLICABILITY

The solid pharmaceutical composition for oral administration provided by the present invention comprises a histamine $H_2$-receptor antagonist and, as antacid components, a low neutralizing capacity antacid and a pH-independent and water-insoluble polymer base-coated high neutralizing capacity antacid and therefore maintains a gastric pH in an optimum range without excessively neutralizing gastric juice immediately after administration over more than half a day. The present invention thus provides a solid pharmaceutical composition for oral administration that improves the condition of a patient promptly after administration and maintains its effects for an extended period of time in the treatment of digestive disorders, such as gastritis, dyspepsia, gastric hyperacidity, heartburn, gastric oppression, and peptic ulcer, on which suppression of gastric acid secretion is deemed effective.

The characteristics of the antacid components in the solid pharmaceutical composition according to the present invention will be demonstrated in the following test examples.

TEST EXAMPLE 1

The chewable tablet obtained in Comparative Example 1 was subjected to an antacid capacity test in artificial gastric juice in accordance with the modified Fuchs method as follows. A coarsely crushed tablet was added to 30 ml of 0.05N hydrochloric acid while stirring at 37° C. Ten minutes later, 0.05N hydrochloric acid was continuously added at a rate of 1 ml/min, and the pH of the test solution was recorded continuously. As the results shown in FIG. 1 reveal, the comparative chewable tablet raised the pH to exceed an optimum level in the initial stage.

TEST EXAMPLE 2

Figure 2:
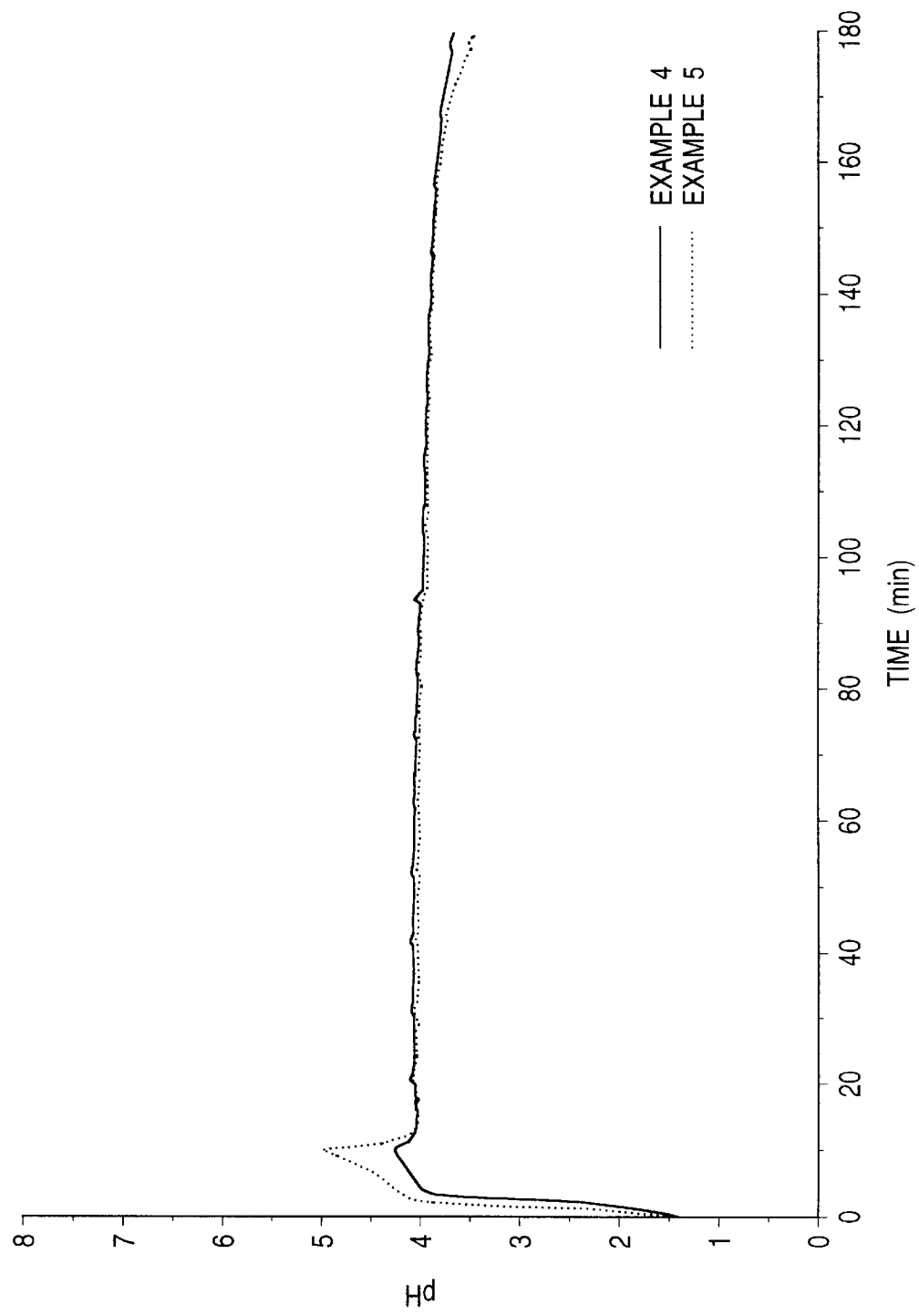
FIG. 2 illustrates the results of testing the antiacid capacity duration of the tablets obtained in Examples 4 and 5 in an artificial gastric juice model according to the modified Fuchs method.

The tablet obtained in Examples 4 and 5 was subjected to an antacid capacity test in the same manner as in Test Example 1. As shown in FIG. 2, the initial rise in pH was controlled, and the optimum pH was sustained for a long period of time in each case.

TEST EXAMPLE 3

Figure 3:
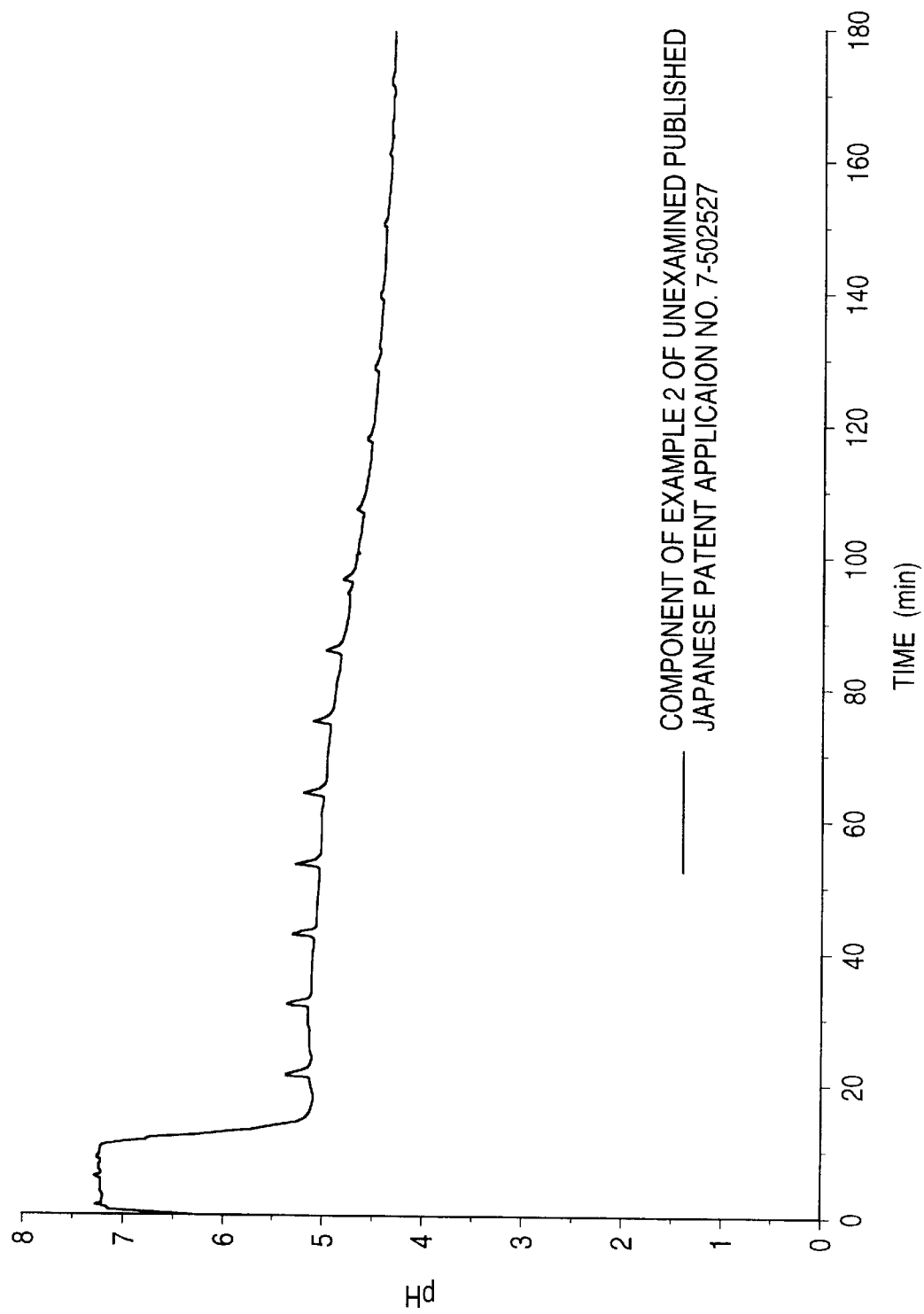
FIG. 3 illustrates the results of testing the antiacid capacity duration of the preparation containing a histamine $H_2$-receptor antagonist and an antacid described in an unexamined published Japanese patent application No. 7-502527 in an artificial gastric juice model according to the modified Fuchs method.

A preparation comprising 2 mg of famotidine, 750 mg of aluminum hydroxide, and 750 mg of magnesium hydroxide and a preparation comprising 1 mg of famotidine, 375 mg of aluminum hydroxide, and 375 mg of magnesium hydroxide which were prepared in accordance with Example 2 of an unexamined published Japanese patent application No. 7-502527 were subjected to the same test. As shown in FIG. 3, either preparation caused a large pH rise in the initial stage up to 7.2, i.e., an alkali region.

What is claimed is:

1. A solid pharmaceutical composition for oral administration which comprises
   (1) a histamine $H_2$-receptor antagonist,
   (2) a low neutralizing capacity antacid, and
   (3) a high neutralizing capacity antacid, said high neutralization capacity antacid being coated with a pH-independent and water-insoluble polymer base.

2. A solid pharmaceutical composition according to claim 1, wherein said histamine $H_2$-receptor antagonist is selected from the group consisting of cimetidine, ranitidine, nizatidine and famotidine or a pharmaceutically acceptable salt thereof.

3. A solid pharmaceutical composition according to claim 2, wherein said histamine $H_2$-receptor antagonist is famotidine.

4. A solid pharmaceutical composition according to claim 1, wherein said antacid having a low neutralizing capacity and said antacid having a high neutralizing capacity give an initial pH of lower than 6 and an initial pH of 6 or higher, respectively, in a test using 30 ml of 0.05N hydrochloric acid and a single dose in accordance with a modified Fuchs method.

5. A solid pharmaceutical composition according to claim 1, wherein said antacid having a low neutralizing capacity and said antacid having a high neutralizing capacity give an initial pH of lower than 6 and an initial pH of 6 or higher, respectively, in a test using 30 ml of 0.05N hydrochloric acid and a single dose in accordance with a modified Fuchs method, said antacid having a low neutralizing capacity and said antacid having a high neutralizing capacity as uncoated are present at a weight ratio of 0.2:1 to 2:1, and the coating weight of said pH-independent and water-insoluble polymer base on said antacid having a high neutralizing capacity is 5 to 100% by weight based on said antacid.

6. A solid pharmaceutical composition according to claim 1, wherein said pH-independent and water-insoluble polymer base is at least one member selected from the group consisting of ethyl cellulose, an aqueous dispersion of ethyl cellulose, an ethyl acrylate-methyl methacrylate copolymer emulsion, and a polyethylacrylate methylmethacrylate trimethylammonioethylmethacrylate chloride.

7. A solid pharmaceutical composition according to claim 1, wherein said antacid having a high neutralizing capacity is at least one member selected from the group consisting of sodium hydrogencarbonate, magnesium oxide, magnesium hydroxide, magnesium carbonate, magnesium silicate, and calcium carbonate.

8. A solid pharmaceutical composition according to claim 1, wherein said antacid having a low neutralizing capacity is at least one member selected from the group consisting of magnesium aluminate, dimagnesium silicate aluminate, magnesium metasilicate aluminate, magnesium bismuth silicate aluminate, synthetic hydrotalcite, dried aluminum hydroxide gel, and aluminum silicate.

9. A solid pharmaceutical composition according to claim 1, which comprises dried aluminum hydroxide gel, magnesium hydroxide, and famotidine.

* * * * *